United States Patent [19]
Kato et al.

[11] Patent Number: 5,314,872
[45] Date of Patent: May 24, 1994

[54] GLUCAN SULFATE, STABILIZED FIBROBLAST GROWTH FACTOR COMPOSITION

[75] Inventors: Koichi Kato, Kawanishi; Kenji Kawahara, Izumi; Tomoko Kajio, Minoo, all of Japan

[73] Assignee: Takeda Chemical Industries, Ltd., Osaka, Japan

[21] Appl. No.: 360,602

[22] Filed: Jun. 2, 1989

[30] Foreign Application Priority Data

Jun. 6, 1988 [JP] Japan .................. 63-138907
Jul. 25, 1988 [JP] Japan .................. 63-185772

[51] Int. Cl.⁵ .................. A61K 37/36; A61K 37/24
[52] U.S. Cl. .................. 514/12; 514/21; 514/23; 514/970; 530/399
[58] Field of Search .................. 514/12, 23, 970, 21; 530/399

[56] References Cited

U.S. PATENT DOCUMENTS 4,717,717 1/1988 Finkenaur .................. 514/21
5,013,714 5/1991 Lindstrom .................. 514/3

FOREIGN PATENT DOCUMENTS 267015 4/1988 European Pat. Off. .
82/0098 1/1982 World Int. Prop. O. .

OTHER PUBLICATIONS

Gospodarowicz et al. J. of Cellular Physiology, 128, 475–484 (1986).
Schreiber et al. Proc. Natl. Acad. Sci. USA, 82, 6138–6142 (1985).
Seno et al. Biochem. Biophys. Res. Commun. 151, 701–708 (1988).
Biotechnology Products Catalog 1993, p. 69.

*Primary Examiner*—F. T. Moezie
*Attorney, Agent, or Firm*—David G. Conlin; Linda M. Buckley

[57] ABSTRACT

Fibroblast growth factor (FGF) or a mutein of FGF is stabilized by bringing FGF or a mutein of FGF into contact with a glucan sulfate in an aqueous medium. Thus obtained composition comprising (a) FGF or a mutein of FGF and (b) a glucan sulfate is stabilized, so that it can be advantageously administered to warm-blooded animals.

15 Claims, 2 Drawing Sheets

```
MetProAlaLeuProGluAspGlyGlySerGlyAlaPheProProGlyHisPheLysAsp         20
ATGCCAGCATTGCCCGAGGATGGCGGCAGCGGCGCCTTCCCGCCGGCCACTTCAAGGAC         60

ProLysArgLeuTyrCysLysAsnGlyGlyPhePheLeuArgIleHisProAspGlyArg         40
CCCAAGCGGCTGTACTGCAAAAACGGGGGCTTCTTCCTGCGCATCCACCCCGACGGCGA        120

ValAspGlyValArgGluLysSerAspProHisIleLysLeuGlnLeuGlnAlaGluGlu         60
GTTGACGGGGTCCGGGAGAAGAGCGACCCTCACATCAAGCTACAACTTCAAGCAGAAGAG      180

ArgGlyValValSerIleLysGlyValValCysAlaAsnArgTyrLeuAlaMetLysGluAsp      80
AGAGGAGTTGTGTCTATCAAAGGAGTTGTGTGCTAACCGTTACCTGGCTATGAAGGAAGAT     240

GlyArgLeuLeuAlaSerLysCysValThrAspGluCysPhePheGluArgLeuGlu          100
GGAAGATTACTGGCTTCTAAATGTGTTACGGATGAGTGTTTCTTTTTGAACGATTGGAA       300

SerAsnAsnTyrAsnThrTyrArgSerArgLysTyrThrSerTrpTyrValAlaLeuLys       120
TCTAATAACTACAATACTTACCGGTCAAGGAAATACACCAGTTGGTATGTGGCACTGAAA     360

ArgThrGlyGlnTyrLysLeuLeuGlyLysSerLysThrGlyProGlyGlnLysAlaIleLeuPhe  140
CGAACTGGGCAGTATAAACTTGGATCCAAAACAGGACCTGGGCAGAAAGCTATACTTTTT     420

LeuProMetSerAlaLysSertrm                                            147
CTTCCAATGTCTGCTAAGAGCTGA                                           444
```

FIG. 1

GLUCAN SULFATE, STABILIZED FIBROBLAST GROWTH FACTOR COMPOSITION

The present invention relates to a stabilized composition of fibroblast growth factor (hereinafter abbreviated FGF) or an FGF mutein, and production thereof.

FGF was first separated as a factor exhibiting strong growth promoting action on fibroblasts such as BALB/c-3T3 cells [Gospodarowicz: Nature, 249, 123 (1974)]. At present, FGF is known to have a growth promoting effect on almost all cells of mesoderm-derived cells. FGF is roughly classified by isoelectric point into two types: basic FGF (hereinafter abbreviated BFGF) and acidic FGF (hereinafter abbreviated aFGF). Having strong growth promoting action and plasminogen activator inducing action on endothelial cells, these types of FGF are expected to have the potential for application as an angiogenesis promoter, a therapeutic drug for trauma, and a preventive and therapeutic drug for thrombosis and arteriosclerosis.

FGF has conventionally been purified, even to the single substance level, from animal organs, e.g. the bovine pituitary gland; however, this conventional method has drawbacks, e.g., there is a quantitative limitation on production, and the obtained FGF may exhibit undesirable antigenicity due to its derivation from a different species. A method of FGF mass-production has recently been developed, wherein recombinant DNA technology is utilized to express a cloned human FGF gene in microorganisms or animal cells [see FEBS Letters, 213, 189-194 (1987) and European Patent Publication No. 237,966].

FGF loses its activity in an aqueous solution rapidly and, in addition, its biological activities often decrease due to lyophilization. In addition, when FGF is administered over a long period, e.g., by intravenous drip infusion, it is inevitable that its potency decreases during the administration period, and this poses a great problem.

It is reported that FGF inactivation can be prevented by the addition of the glycosaminoglycan, heparin [Journal of Cellular Physiology, 128, 475 (1986)], but heparin is difficult for use in injections, etc., because it has a strong anticoagulation activity.

With the aim of improving the stability of FGF in a solution or under lyophilizing conditions, various substances generally formulated into injections have been investigated. However, no satisfactory method of stabilization has been found so far; such a method remains to be developed.

Taking note of these circumstances, the present inventors conducted investigations and found that the stability of FGF or an FGF mutein, unexpectedly, is noticeably increased by bringing FGF or an FGF mutein into contact with glucan sulfate such as dextran sulfate in an aqueous solution. The inventors made further investigations based on this finding, and developed the present invention.

SUMMARY OF THE INVENTION

The present invention is directed to (1) a stabilized composition which comprises (a) FGF or a mutein of FGF and (b) a glucan sulfate; (2) a method for producing a stabilized composition of FGF or a mutein of FGF, which comprises bringing said FGF or mutein of FGF into contact with a glucan sulfate in an aqueous medium; and (3) a method for stabilizing FGF or a mutein of FGF, which comprises bringing said FGF or mutein of FGF into contact with a glucan sulfate in an aqueous medium.

The FGF used for the present invention may be a basic FGF or an acidic FGF.

As examples of the FGF for the present invention, mention may be made of mammal-derived FGF. Examples of mammals include humans, monkeys, swine, bovines, sheep and horses.

Examples of said FGF include but are not limited to FGF extracted from various organs which have already been found to contain FGF, such as the brain or the pituitary gland or the FGF produced by recombinant DNA technology.

As an example of said FGF, mention may also be made of the FGF obtained by recombinant DNA technology as shown in PCT International Publication No. WO/87/01728; FEBS Letters, 213, 189-194 (1987); European Patent Publication No. 237,966.

In the present specification, recombinant human basic FGF is sometimes abbreviated to rhbFGF.

The term "FGF mutein", i.e. mutein of FGF, as it is used in this application is defined as a protein having a degree of amino acid sequence homology with FGF and which exhibits pharmacological or physiological activities similar to those of FGF.

The FGF mutein for the present invention essentially has an amino acid sequence resulting from variation of the sequence of the original peptide or protein; such variations include amino acid addition, constituent amino acid deletion, and constituent amino acid substitution by other amino acid.

Such addition of amino acid includes addition of at least one amino acid.

Such deletion of constituent amino acid includes deletion of at least one bFGF-constituent amino acid.

Such substitution of constituent amino acid by other amino acids includes substitution of at least one bFGF-constituent amino acid by other amino acid.

The at least one amino acid in the mutein which has at least one amino acid added to BFGF excludes methionine deriving from the initiation codon used for peptide expression and signal peptide.

The number of added amino acids is at least 1, but it may be any one, as long as BFGF characteristics are not lost. Preferable amino acids should include some or all of the amino acid sequences of proteins which have homology with BFGF and which exhibit activities similar to those of BFGF.

As for the number of deleted bFGF-constituent amino acids in the present mutein which lacks at least 1 bFGF-constituent amino acid, it may be any one, as long as any characteristic of BFGF is not lost.

As examples of such deleted constituent amino acids, mention may be made of: the deletion of amino acids from amino terminal or carboxyl terminal; the 10 residues in the amino terminal of human BFGF:

Met-Pro-Ala-Leu-Pro-Glu-Asp-Gly-Gly-Ser the 14 residues in the amino terminal of human BFGF:

Met-Pro-Ala-Leu-Pro-Glu-Asp-Gly-Gly-Ser-Gly-Ala-Phe-Pro the 41 residues in the amino terminal of human BFGF:

```
  1    2    3    4        41
 Met—Pro—Ala—Leu— ... —Val
``` or the 61 residues in the carboxyl terminal of human BFGF:

```
        87   88        146  147
        Lys—Cys— ... —Lys—Ser
``` is deleted.

The FGF mutein of the present invention also includes muteins of bFGF in which from 7 to 46 amino acid residues have been deleted from the carboxyl terminal.

As examples of the preferred amino acid deletions, mention may be made of the amino acid sequences respectively starting at rhbFGF amino acid Nos. 102, 106, 115, 119, 124, 130 or 138.

These -amino acid sequences may be replaced by another amino acid.

As for the number of at least 1 bFGF-constituent amino acids before substitution in mutein which has at least 1 bFGF-constituent amino acid substituted by other amino acids, it may be any one, as long as any characteristic of BFGF is not lost.

As examples of constituent amino acids before substitution, mention may be made of cysteine and amino acids other than cysteine. Cysteine is preferable. As the constituent amino acid other than cysteine before substitution, there may be mentioned aspartic acid, arginine, glycine, serine, valine and so forth.

When the constituent amino acid before substitution is cysteine, for substituted amino acids are preferably, for example, neutral amino acids. As specific examples of such neutral amino acids, mention may be made of glycine, valine, alanine, leucine, isoleucine, tyrosine, phenylalanine, histidine, tryptophan, serine, threonine and methionine. Specifically, serine and threonine are preferable.

When the constituent amino acid before substitution is any one other than cysteine, for other substituted amino acids are selected amino acids which are different from the amino acid before substitution in a property such as hydrophilicity, hydrophobicity or electric charge.

When the constituent amino acid before substitution is aspartic acid, substituted amino acids include asparagine, threonine, valine, phenylalanine and arginine; asparagine and arginine are preferable.

When the constituent amino acid before substitution is arginine, substituted amino acids include glutamine, threonine, leucine, phenylalanine and aspartic acid; glutamine is preferable.

When the constituent amino acid before substitution is glycine, substituted amino acids include threonine, leucine, phenylalanine, serine, glutamic acid, and arginine; threonine is preferable.

When the constituent amino acid before substitution is serine, substituted amino acids include methionine, alanine, leucine, cysteine, glutamine, arginine and aspartic acid; methionine is preferable.

When the constituent amino acid before substitution is valine, substituted amino acids include serine, leucine, proline, glycine, lysine, and aspartic acid; serine is preferable.

As the constituent amino acid before substitution, aspartic acid, arginine, glycine, serine and valine are preferred.

As the substituted amino acid, asparagine, glutamine, arginine, threonine, methionine, serine, and leucine are preferred.

As the preferred embodiment on the substitution in the mutein, a substitution of serine for cysteine (i.e. cysteine is replaced by serine) is most preferred.

In said substitution, not less than 2 substitutions may be occurred, and two or three substitutions are preferred.

The mutein of the present invention may be a combination of 2 or 3 of the above-mentioned additions, deletions and substitutions.

As the mutein, muteins wherein at least one of the constituent amino acid of human basic FGF has been replaced by other amino acid are preferred.

In addition to conventional DNA recombination techniques, site-directed mutagenesis may be employed to produce the mutein of the present invention. The said technique is well-known, and it is described in Genetic Engineering, Lather, R. F. and Lecoq, J. P., Academic Press, pp. 31 to 50 (1983). Mutagenesis directed to oligonucleotides is described in Genetic Engineering: Principles and Methods, Smith, M. and Gillam, S., Plenum Press, Vol. 3, pp. 1 to 32 (1981).

The production of the structural gene which encodes the mutein of the present invention is, for example, carried out by: (a) hybridizing with a mutagenic oligonucleotide primer a single-stranded DNA comprising 1 strand of the structural gene of FGF (Said primer is complementary to a region of the strand which includes the codon for the cysteine to be replaced or to a region of the antisense triplet paired with the codon, except for a mismatch with that codon and a codon for the other amino acid, and as the case may be, with that codon and antisense triplet codon.), (b) elongating the primer using DNA polymerase to form a mutational heteroduplex, and (c) replicating this mutational heteroduplex.

The DNA carrying the mutational gene is then isolated, and incorporated in a plasmid.

Using the plasmid, a host cell is transformed to give a transformant.

Said transformant is cultivated in a culture medium to allow it to produce mutein.

Examples of the FGF muteins used for the present invention include the muteins described in Biochemical and Biophysical Research Communications, 151, 701–708 (1988which corresponds to U.S. patent application Ser. No. 07/301,460) European Patent Publication No. 281,822, which corresponds to U.S. patent application Ser. No. 07/301,460, European Patent Publication No. 288,687 (European Patent Application No. 88103047.2) which corresponds to Japanese Patent Application No. 50249/1988 and to U.S. patent application Ser. No. 07/157,453, European Patent Application No. 89101162.9 (filed on Jan. 24, 1989which corresponds to U.S. patent application Ser. No. 07/301,460).

Examples of glucan sulfate employable in the present invention include dextran sulfate, cyclodextrin sulfate, and β-1,3-glucan sulfate. Said glucan sulfate is a sulfuric ester derivative of a polymer of D-glucose. Said glucan sulfate preferably has sulfur content of not less than about 3% (W/w), more preferably has sulfur content of about 12 to 20% (w/w), and still more preferably has sulfur content of about 16 to 20% (w/w). In particular, dextran sulfate is preferred.

Examples of the dextran sulfate employable in the present invention include sulfate of dextran, the dextran being produced from sucrose by the action of microorganisms such as *Leuconostoc mesenteroides*. Dextran sulfate is a sulfate of dextran whose principal structure is α(1→6) linkage, and the sulfur content is usually not less than about 12%, preferably about 16 to 20%. Average molecular weight is in the range of from about 1,000 to 40,000,000, preferably in the range of from about 3,000 to 1,000,000, and the dextran sulfate is very soluble in water. Dextran sulfate is a known compound, and can be produced by per se known method.

Examples of cyclodextrin for the cyclodextrin sulfate for the present invention include the cyclodextrin produced from starch by action of microorganisms such as *Bacillus macerans*. Cyclodextrin, a ring structure of D-glucose molecules linked by α (1→4) linkage, is divided by the number of ring-forming D-glucose molecules into various types: α-type (6 molecules), β-type (7 molecules), γ-type (8 molecules), and others. An of these types can be used for the present invention.

Cyclodextrin sulfate is an ester resulting from the sulfation of these cyclodextrins, and this sulfation is carried out in accordance with an already known method. Examples of the method of sulfation includes methods described in U.S. Pat. No. 2,923,704 and Japanese Patent Application Laid-open No. 36422/1975.

The sulfur content of cyclodextrin sulfate normally exceeds 3% (W/W), preferably at about 12 to 24% (W/W). Cyclodextrin sulfate has a characteristic that it is very soluble in water.

The degree of sulfation of cyclodextrin sulfate for the present invention may be at any level exceeding 12% (W/W) as calculated as sulfur content; in particular, cyclodextrin sulfate containing about 16 to 21% (W/W) sulfur is advantageous. Furthermore, mixtures of cyclodextrin sulfates with different degrees of sulfation may be used, and a single cyclodextrin sulfate obtained by purification to a single degree of sulfation may also be used. The purification can, e.g., be achieved by concentrating to dryness a reaction mixture containing an alkali metal salt of cyclodextrin sulfate, dissolving the resulting concentrate in water and mixing this aqueous solution with a hydrophilic solvent to separate the desired product.

Examples of β-1, 3-glucan for the β-1, 3-glucan sulfate for the present invention include straight chain β-1, 3-glucan produced by microorganisms belonging to the genus Alcaligenes or Agrobacterium. The β-1, 3-glucan may also be in the form of a low molecular weight polymer having a straight β-1, 3-glucan structure as is well obtained by hydrolysis of straight chain β-1, 3-glucan.

Curdlan (also known as thermogelable polysaccharide PS, commercially available from Wako Pure Chemical Industries, Ltd.) is known to be a water-insoluble, thermogelable, unbranched glucan which has straight chain β-1, 3- glucan linkage alone and which is produced by microbial strains belonging to the genus Alcaligenes or Agrobacterium [Japanese Patent Publication Nos. 7,000/1968, 32,673/1973 and 32,674/1973]. The curdlan producers *Alcaligenes faecalis* var. myxogenes NTK-u strain, *Agrobacterium radiobacter* strain and *Agrobacterium radiobacter* U-19 strain are listed respectively under ATCb-21680, ATCC-6466 and ATCC-21679 in the American Type Culture Collection Catalogue of Strains, I, 15th edition, 1982.

Properties of the partial hydrolysate (low molecular weight derivatives) of curdlan and a method of its production are already described in detail in Japanese Patent Application Laid-open No. 83798/1980.

Accordingly, said direct chain β-1, 3-glucan is a compound represented by the formula:

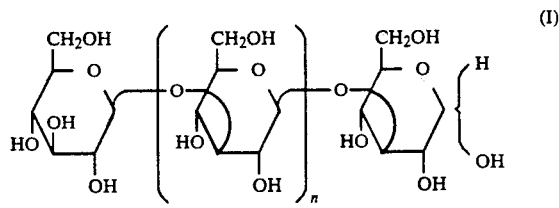

where n represents an integer of from 4 to about 1000.

The above-mentioned β-1, 3-glucan may have any average degree of polymerization (DP) below 1000. In particular, its partial hydrolysate with a DP ranging from 6 to about 300 is recommended, and its partial hydrolysate with a DP from 15 to about 200 is preferred.

Note that n and DP in formula (I) bear the relation of DP-2 =n.

The sulfate of straight chain β-1, 3-glucan for the present invention is an ester resulting from the sulfonation of three hydroxyl groups in intermediate monosaccharide and the hydroxyl groups in the terminal monosaccharide units in any of these β-1, 3-glucan or its lower polymers; an ester with an average degree of substitution (DS) of 0.5 to 3 per monosaccharide unit is nominally used, and an ester with a DS of 1 to 2 is preferably used.

Sulfation of straight chain β-1, 3-glucan or its low molecular weight polymer can be achieved by allowing a sulfating agent, such as chlorosulfonic acid or a complex of sulfuric anhydride and an organic base, such as pyridine, dimethylformamide, trimethylamine or dimethylaniline therewith to act on the β-1, 3-glucan [Journal of Biological Chemistry, 239, 2986 (1964)].

The β-1, 3-glucan sulfate used for the present invention is very soluble in water, with low toxicity.

The sulfur content of β-1, 3-glucan sulfate is normally over 5% (W/W), preferably about 10 to 24% (W/W), and it is very soluble in water.

The glucan sulfate used for the present invention shows very low toxicity to warm-blooded animals, therefore, the composition of FGF or an FGF mutein for the present invention has an advantage that it can be safely administered orally or parenterally to warm-blooded animals.

The glucan sulfate employable in the present invention may be in the free state or in the form of a salt. As the salt, there may be mentioned, for example, sodium salt, potassium salt, ammonium salt, trimethyl ammonium salt, etc.

When bringing glucan sulfate into contact with FGF or an FGF mutein in an aqueous medium, it may be conducted by first adding glucan sulfate in the free state then by adding an adequate amount of an alkali or an acid to adjust the pH. By the addition of an alkali, the dextran sulfate may take the form of a salt in the aqueous medium, or a mixture of free dextran sulfate and glucan sulfate in the salt form may coexist.

When the FGF or an FGF mutein of the present invention is brought into contact with glucan sulfate in an aqueous medium, it is preferably conducted in the presence of di- or tri-basic carboxylic acid to give more stabilized FGF or an FGF mutein.

Examples of the di-basic carboxylic acid include tartaric acid, maleic acid, malic acid, fumaric acid, etc.

Examples of the tri-basic carboxylic acid include citric acid, iso-citric acid, etc.

The above-mentioned carboxylic acids may be free ones or in the form of a salt. It may also be possible that free carboxylic acid is added to an aqueous medium, to which is added an adequate amount of an alkali or an acid to adjust the pH.

The amount of the carboxylic acid is preferably such as its concentration in an aqueous medium ranges from 1 mM to 1M, more preferably from about 10 mM to 500 mM.

When FGF or an FGF mutein is brought into contact with dextran sulfate in an aqueous medium, the amount of glucan sulfate ranges from about 0.1 to 100 mol., more preferably, from about 0.5 to 4 mol. relative to 1 mol. of FGF or an FGF mutein.

The concentration of dextran sulfate in an aqueous medium ranges preferably from about 0.0005 to 5 w/v%, more preferably from about 0.01 to 1 W/V %.

The concentration of FGF in an aqueous medium ranges preferably from about 0.0005 to 5 w/v %, more preferably from about 0.01 to 1 W/V %.

For bringing FGF or an FGF mutein into contact with glucan sulfate and further with carboxylic acid in an aqueous medium, mere mixing of these materials in the aqueous medium accomplishes the purpose.

As the aqueous medium, any aqueous medium for injection can be used; in particular, distilled water for injection, physiological saline, and glucose solution are preferably used. Buffers, such as phosphate buffer and Tris-hydroxymethyl-aminomethane-HCl buffer, can also be used as the aqueous medium in the present invention.

When FGF or an FGF mutein, glucan sulfate and carboxylic acid are mixed, they may be in the state of aqueous solutions, respectively, or a mixture of these materials in solid form may be dissolved in water. The mixing of these materials is conducted at temperatures ranging from 0° to 40° C. and preferably at pH ranging from about 3 to 10, more preferably from about 5 to 9. The time required for the mixing is usually in the range of from about 1 to 30 minutes.

By the processes as described above, a stabilized composition of FGF or an FGF mutein can be obtained.

It is confirmed that in said stabilized composition of FGF or an FGF mutein, FGF or an FGF mutein and glucan sulfate associate at a certain ratio to form a complex; the complex of FGF or an FGF mutein can be isolated as desired. Examples of methods of isolation and collection include gel filtration with Sephadex or TSK gel, ion exchange chromatography using DEAE- or CM-Toyopearl, and isoelectric fractionation. Accordingly, the complex of FGF or an FGF mutein may be isolated and collected as desired, or may be used as the composition without isolation.

The complex thus obtained is a complex formed by FGF or an FGF mutein and glucan sulfate at a ratio of about 1:0.5 to about 1:5. Note that said complex dissociates in the presence of a high concentration of salt, e.g. 1M NaCl; the use of a solvent with high ionic strength must be avoided during the isolation procedure.

A composition of stabilized FGF or an FGF mutein is thus obtained. Accordingly, as shown in the working examples presented below, the composition of the present invention is stable regarding heat, pH and proteases.

In particular, the composition of the present invention is stable under acidic and alkaline conditions, as well as under neutral conditions.

The composition of FGF or an FGF mutein can be safely administered orally or parenterally to warmblooded animals (e.g. humans, mice, rats, hamsters, rabbits, dogs, cats) directly or in a pharmaceutical composition (e.g. injection, tablets, capsules, solutions, ointments) with pharmacologically acceptable carriers, excipients or diluents.

It is preferable that said preparation be in the form of injection, solution for injection, frozen preparation or lyophilized preparation, for instance.

In formulating said composition into a pharmaceutical composition, pharmacologically acceptable additives, diluents, excipients, etc. can be used in accordance with known methods of pharmaceutical production as desired.

When the composition is formulated into an injectable aqueous solution, for instance, the desired solution is prepared by a standard method using a solvent such as an aqueous solvent (e.g. distilled water), water-soluble solvent (e.g. physiological saline, Ringer's solution), or oily solvent (e.g. sesame oil, olive oil) or, as desired, an additive such as a dissolution aid (e.g. sodium salicylate, sodium acetate), buffer (e.g. sodium citrate, glycerine), isotonizing agent (e.g. glucose, invert sugar), stabilizer (e.g. human serum albumin, polyethylene glycol), preservative (e.g. benzyl alcohol, phenol) or analgesics (e.g. benzalkonium chloride, procaine hydrochloride).

When said composition is formulated into a solid preparation for injection, for instance, the desired preparation can be produced by a routine method using diluents (e.g. distilled water, physiological saline, glucose), excipient (e.g. carboxymethyleellulose (CMC), sodium arginate), preservatives (e.g. benzyl alcohol, benzalkonium chloride, phenol), or analgesics (e.g. glucose, calcium gluconate, procaine hydrochloride).

Furthermore, in formulating said composition into a pharmaceutical preparation, monosaccharides (e.g. glucose), amino acids, various salts and human serum albumin may be added; isotonizing agents, pH regulators, analgesics, antiseptics, and other compounds, etc. may also be added to prepare a stable and effective preparation of FGF or an FGF mutein.

The composition of FGF or an FGF mutein obtained by any one of the above-mentioned methods has fibroblast growth promoting action and other actions and is very stable and low in toxicity; therefore, it can be used as a healing promoter for damaged or diseased tissue, such as burns, wounds, postoperative tissues or, based on its angiogenic action, as a therapeutic drug for thrombosis and arteriosclerosis.

Thus stabilized composition can also be used as an agent for treating mammals having a disease which is FGF-response, or for treating mammals having an ulcerating disease of the gastrointestinal tract (U.S. patent application Ser. No. 234,966).

The composition of FGF or an FGF mutein according to the present invention, when used as any of the above-mentioned pharmaceuticals, is, for example, administered to the above-mentioned warm-blooded animals in an appropriate amount chosen in the range from about 1 $\mu$g/kg to 100 $\mu$g/kg daily, calculated as the dose of FGF or an FGF mutein, taking note of the route of administration, symptoms, etc.

The composition can also be used as a reagent for accelerating cell growth. The composition of FGF or an FGF mutein according to the present invention, when used in this way, is preferably added to the cell growth medium so that it is contained therein in an amount of about 0.01 to 10 μg per liter, more preferably about 0.1 to 10 μg per liter of medium, as calculated as the amount of FGF or an FGF mutein.

Since FGF or an FGF mutein can be stabilized by bringing it into contact with glucan sulfate in an aqueous medium as described above and stabilized composition of FGF or an FGF mutein can be thus obtained, it is possible to formulate FGF or an FGF mutein into a pharmaceutical preparation while sustaining its effect stably.

In addition, the anticoagulation action of glucan sulfate poses no problem in administering the composition of the present invention, because it is a weaker anticoagulant than heparin.

By bringing FGF or an FGF mutein into contact with glucan sulfate in an aqueous medium, stabilized composition of FGF or an FGF mutein can be obtained. Thus stabilized composition of FGF or an FGF mutein can be formulated into pharmaceutical preparations while having the effect of FGF or an FGF mutein.

BRIEF EXPLANATION OF THE DRAWINGS

FIG. 1 shows the base sequence which encodes human BFGF and the amino acid sequence deduced therefrom.

Figure 2:
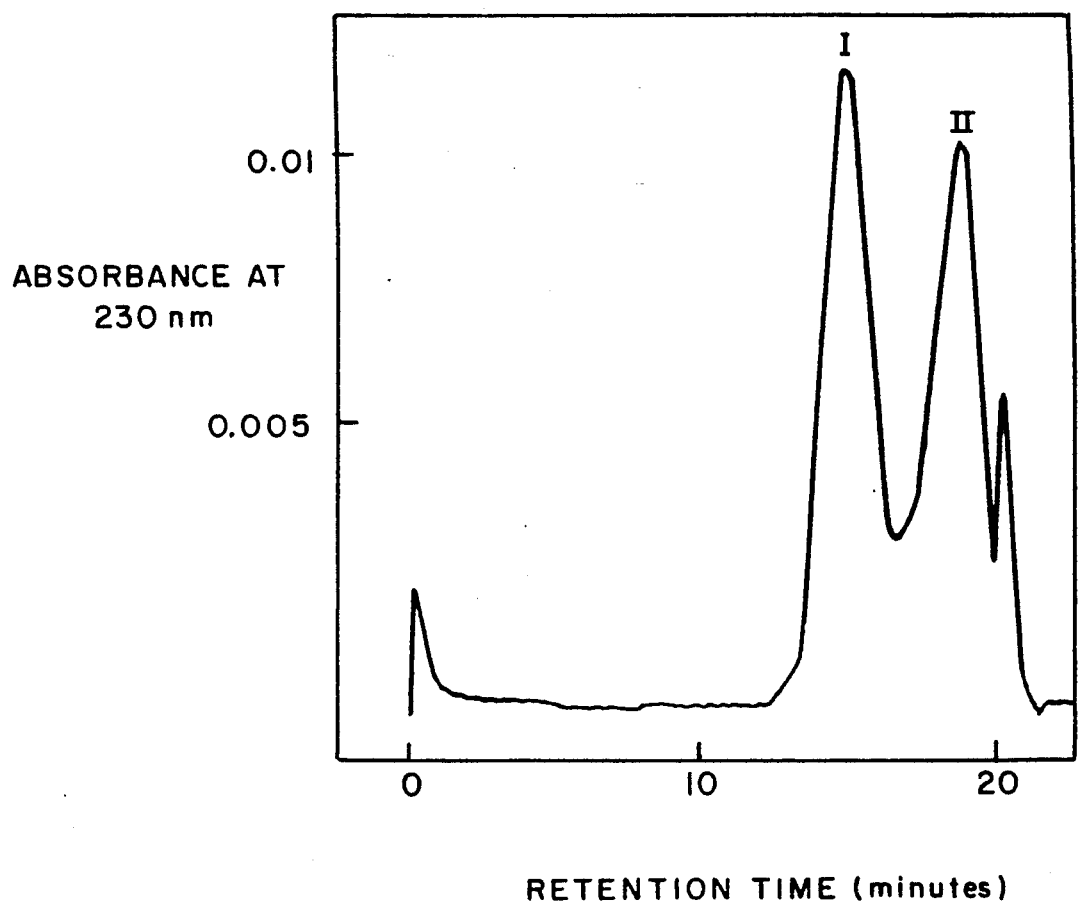
FIG. 2 shows the gel filtration pattern of the composition of rhbFGF mutein CS23 and low molecular weight heparin obtained in Example 12.

The recombinant human basic FGF (hereinafter also abbreviated rhb FGF) used in the working examples presented below is produced by the method described in European Patent Publication (hereinafter also referred to as EP Publication) No. 237,966 which corresponds to U.S. patent application Ser. No. 07/629,058. Accordingly, said rhbFGF is produced and purified by the method described in Examples 1, 3, and 6 or 8 of EP Publication No. 237,966, which corresponds to U.S. patent application Ser. No. 07/629,058 using the transformant *Escherichia coli* K12 MM294/pTB669 (IFO 145311-FERM BP-1281).

The recombinant human basic FGF mutein CS23 (hereinafter also referred to as rhbFGF mutein CS23) used in Examples presented below is produced by the methods described in Examples 7 and 24 of EP Publication No. 281,822, which corresponds to U.S. patent application Ser. No. 07/301,460. Reference Examples 10 of EP Publication No. 288,687 (EP Application No. 88103047.2) which corresponds to Japanese Patent Application No. 50249/1988, and to U.S. patent application Ser. No. 07/157,453 or Biochemical and Biophysical Research Communications, 151, 701–708 (1988). Accordingly, said rhbFGF mutein CS23 has been produced and purified by the methods described in Reference Examples 1 through 3 presented below (methods are the same as those described in the above-mentioned references) using the transformant *Escherichia coli* MM294/pTB762 (IFO 14613, FERM BP-1645).

The above-mentioned transformants *E. coli* K12 MM294/pTB669 (harboring the plasmid pTB669 used in Reference Example 1 below) and *E. coli* MM294/pTB762 (see Reference Example 3 below) have been deposited at the Institute for Fermentation, Osaka (IFO), Japan and at the Fermentation Research Institute, Agency of Industrial Science and Technology, Ministry of International Trade and Industry (FRI), Japan. Their accession numbers and dates of deposition are shown in Table 1. As for the deposition at the FRI, depositions were initially made under accession numbers denoted by FERM P numbers. Said depositions were converted to depositions under the Budapest Treaty and the transformants have been stored at the institute (FRI) under accession numbers denoted by FERM BP numbers.

TABLE 1

| Transformant | IFO | FRI |
|---|---|---|
| *E. coli* K12 MM294/ pTB669 | IFO 14532 (August 11, 1986) | FERM P-8918 FERM BP-1281 (August 21, 1986) |
| *E. coli* MM294/ pTB762 | IFO 14613 (May 27, 1987) | FERM P-9409 FERM BP-1645 (June 11, 1987) |

In numbering the amino acids in human BFGF amino acid sequences described above or in the following reference examples, the Met at the NO terminal of the human BFGF amino acid sequence shown in FIG. 1 is determined as the first amino acid.

REFERENCE EXAMPLE 1

Production of recombinant DNAs containing mutein-encoding base sequences (1) Cloning of M13 vector of human BFGF gene The plasmid pTB669 obtained in Example 3 of European Patent Publication No. 237,966, which corresponds to U.S. patent application Ser. No. 07/629,058 was digested with the restriction enzymes EcoR I and BamH I. The phage vector M13mp8 [J. Messing, Methods, in Enzymology, 101, 20–78 (1983)] replicative-form (RF) DNA was digested with the restriction enzymes EcoR I and BamH I, and was mixed with the human bFGF DNA fragment deriving from the digested pTB669. The mixture was then ligated together by means of T4 DNA ligase; the ligated DNA was transformed into competent cells of the strain *Escherichia coli* JM105; the resulting transformants were inoculated onto a plate using Xgal (5-bromo-4F) chloro-3-indolyl-β-D-galactopyranoside) as an indicator [J. Messing et al., Nucleic Acids Research, 9, 3007 021 (1981)]; the plaques containing the recombinant phage (white plaque) were picked up; the base sequence of the recombined region was determined by the dideoxynucleotide synthetic chain termination method [J. Messing et al., Nucleic Acids Research, 9, 309 (1981)] whereby it was confirmed that human BFGF DNA had been accurately inserted.

From this M13-P0 clone was purified a single-stranded phage DNA, which was then used as a template for site-directed mutagenesis using a synthetic oligonucleotide, by any of the following procedures.

(2) Site-specific mutagenesis

In the presence of 0.1 mM adenosine triphosphate (ATP), 50 mM Tris (hydroxymethyl)aminomethane hydrochloride (Tris-HCl, pH 8.0), 10 mM MgCl$_2$, 5mM dithiothreitol (DTT) and 9 units of T4 kinase, in a total amount of 50 μl, 40 picomoles of the synthetic oligonucleotide:

5'>CGT TCT TGC TGT AGA GCC GCT<3'

[primer for changing Cys 26 to Ser (the recognition sequence for the restriction enzyme Rsa I disappears.)] was treated with T4 kinase at 37° C. for 1 hour. This kinase-treated primer (12 picomoles) was heated at 67° C. for 5 minutes, and at 42° C. for 25 minutes, in 50 μl of a mixture containing 50 mM NaCl, 1.0 mM Tris-HCl (pH 8.0), 10 mM MgCl$_2$ and 10 mM β-mercaptoethanol, whereby the primer was hybridized to 5 μg of the single-stranded (ss) M13-PO DNA. The annealed mixture was then cooled on ice, and it was added to 50 μl of a reaction mixture containing 0.5 mM deoxynucleotide triphosphate (dNTP), 80 mM Tris-HCl (pH 7.4), 8 mM MgCl$_2$, 100 mM NaCl, 9 units of DNA polymerase I Klenow fragment, 0.5 mM ATP and 2 units of T4 DNA ligase, and reaction was carried out at 37° C. for 3 hours, and at 25° C. for 2 hours, whereafter the reaction was stopped by adding 2 μl of 0.2 mM EDTA. The reaction product was used to transform competent JM 105 cells; the transformant cells thus obtained were allowed to grow overnight, whereafter ssDNA was isolated from the culture medium supernatant. Using this ssDNA as a template for the 2nd cycle of primer elongation, gel-purified RF-type DNA was transformed into competent JM 105 cells; the resulting transformant cells were spread over an agar plate, and were cultured overnight to obtain phage plaques.

(3) Site-directed mutagenesis

The procedure of the above term (2) was repeated but the used synthetic oligonucleotide primer was:

5'>AAC GAT TAG CGC TCA CTC C<3' which so changes the cysteine-70-encoding codon that the codon encodes serine. (A recognition sequence of the restriction enzyme Hae II was produced.)

(4) Site-directed mutagenesis

The procedure of the above term (2) was repeated but the used synthetic oligonucleotide primer was:

5'>GTA ACA GAC TTA GAA GCT AGT<3' which so changes the cysteine-88-encoding codon that the codon encodes serine. (A recognition sequence for the restriction enzyme Hae II was produced.)

(5) Site-directed mutagenesis

The procedure of the above term (2) was repeated but the used synthetic oligonucleotide primer was:

5'TCG AAG AAG AAA GAC TCA TCC<3' which so changes the cysteine-93-encoding codon that the codon encodes serine. (A recognition sequence for the restriction enzyme Hint I was produced.))

(6) Screening and identification of plaques made mutagenic

Plates containing mutated M13-PO plaques [above term (1)] and 2 plates containing unmutated M13-PO phage plaques were cooled to 4° C., and the plaques from each plate were transferred to 2 round nitrocellulose filters by keeping a dry filter placed on the agar plate for 5 minutes in the case of the 1st filter, and for 15 minutes in the case of the 2nd filter. The filters were then kept placed for 5 minutes on thick filter papers immersed in 0.2N NaOH, 1.5M NaCl and 0.2% Triton X-100, after which they were neutralized by keeping them placed for 5 more minutes on filter papers immersed in 0.5M Tris-HCl having a ph-value of 7.5 and 1.5M NaCl. The filters were twice washed on filters immersed in 2×SSC (1×SSC is 0.15M sodium chloride and 0.15M sodium citrate) in the same manner, and were allowed to dry, and this was followed by drying at 80° C. for 2 hours in a vacuum oven. These filters were subjected to prehybridization at 55° C. for 4 hours with 10 ml/filter of a DNA hybridization buffer solution (5×SSC) having a ph-value of 7.0 containing 4×Denhardt's solution (polyvinylpyrrolidone, Ficoll and bovine serum albumin, 1×=0.02%), 0.1% sodium dodecyl sulfate (SDS), 50 mM sodium phosphate-buffered solution having a ph-value of 7.0 and 100 μg/Ml denatured salmon sperm DNA. Hybridization was carried out at 42° C. for 24 hours with $10^5$ cpm/ml of an oligonucleotide primer. The filters were each washed in a buffer solution containing 0.1% SDS and 2×SSC at 50° C. for 30 minutes. The filters were then first washed with a buffer solution containing 2×SSC; the control filters, which contained unmutated M13-PO plaques, were examined for radioactivity using a Geiger counter. While stepwise reducing SSC concentration, the control filters were washed until no detectable radioactivity remained on the filters. The minimum of the used SSC concentrations was 0.1×SSC. The filters were allowed to dry in air, and autoradiographs were taken by 2 to 3 days of exposure at −70° C. Screening was carried out of 10,000 mutated M13-PO plaques and 100 unmutated control plaques using a kinase-treated oligonucleotide probe. None of the control plaques hybridized to the probe, while 3 to 10 of the mutated M13-PO plaques hybridized to the probe.

Several of the mutated M13-PO plaques were taken, and transformed into competent JM105 cells. From the supernatant, ssDNAs were prepared, and from the bacterial cell pellets double-stranded (ds) DNAs were prepared. Analyses were made of the base sequences using appropriate oligonucleotide primers and ssDNAs.

As a result, it was respectively confirmed that mutant phage strains had been obtained in which the TGC (Cys-26) codon had been changed to a TCT (Ser) codon; the TGT (Cys-70) codon, to an AGC (Ser) codon; the TGT (Cys-88) codon, to a TCT (Ser) codon; and the TGT (Cys-93) codon, to a TCT (Ser)codon.

Of these phage strains, the phage in which the codon Cys-26 had become a Ser-encoding codon was named M13-P1; the phage in which the codon Cys-70 had become a Ser-encoding codon, M13-P2; the phage in which the codon Cys-88, M13-P3; and the phage in which the codon Cys-93 had become a Ser-encoding codon, M13-P4.

REFERENCE EXAMPLE 2

Screening and identification of plaques which were made mutagenic

Plates containing mutated M13-P2 phage plaques obtained in Reference Example 1 and two plates containing unmutated M13-PO phage plaques obtained in Reference Example 1 were cooled to 4° C., and the plaque from each plate was transferred to 2 round nitrocellulose filters by keeping a dry filter placed on the agar plate for 5 minutes in the case of the 1st filter, and for 15 minutes in the case of the 2nd filter. The filters were then kept placed for 5 minutes on thick filter papers immersed in 0.2N NaOH, 1.5M NaCl and 0.2% Triton X-100, after which they were neutralized by keeping them placed for 5 more minutes on filter papers immersed in 0.5M Tris-HCl (pH 7.5) and 1.5M NaCl. The filters were twice washed on filters immersed in 2×SSC in the same manner, and were allowed to dry, and this was followed by drying at 80° C. for 2 hours in a vacuum oven. These filters were subjected to prehybridization at 55° C. for 4 hours with 10 me/filter of a DNA hybridization buffer solution (5×SSC) having a ph-value of 7.0 containing 4×Denhardt's solution, 0.1% sodium dodecyl sulfate, 50 mM sodium phosphate-buffered solution having a ph-value of 7.0 and 100 μg/ml denatured salmon sperm DNA. Hybridization was carried out at 42° C. for 24 hours with $10^5$ cpm/ml of an oligonucleotide primer. The filters were each washed in a buffer solution containing 0.1% SDS and 2×SSC at 50° C. for 30 minutes. The filters were then first washed with a buffer solution containing 2×SSC; the control filters, which contained unmutated M13-P2 plaques, were examined for radioactivity using a Geiger counter. While stepwise reducing SSC concentration, the control filters were washed until no detectable radioactivity remained on the :filters. The minimum of the used SSC concentrations was 0.1 ×SSC. The filters were allowed to dry in air, and radioautographs were taken by 2 to 3 days of exposure at −70° C. Screening was carried out of 10,000 mutated M13-P2 plaques and 100 unmutated control plaques using a kinase-treated oligonucleotide probe. None of the control plaques hybridized to the probe, while 3 to 10 of the mutated M13-P2 plaques hybridized to the probe.

One of the mutated M13-P2 plaques was taken, and was transformed into competent JM105 cells. From the resulting supernatant an ssDNA was prepared, and from the bacterial cell pellets double-stranded (ds) DNA was prepared. Analyses were made of the base sequences using appropriate oligonucleotide primers and ssDNAs.

As a result, it was respectively confirmed that in addition to the Cys-70 substitution, the TGC (Cys-26) codon had been changed to a TCT (Ser) codon; the TGT (Cys-88) codon, to a TCT (Ser) codon; and the TGT (Cys-93) codon, to a TCT (Ser) codon.

Of the mutated M13-P2 phages, the phage in which the codons Cys-26 and −70 had become Ser-encoding codons was named M13-P12; the phage in which the codons Cys-70 and -88 had become Ser-encoding codons, M13-P23; and the phage in which the codons Cys-70 and -93 had become Ser-encoding codons, M13-P24.

REFERENCE EXAMPLE 3

Expression in Escherichia coli of gene encoding human BFGF mutein (1) Construction of the plasmid pTB762 for human BFGF mutein expression The M13-P23 replicative form (RF) obtained in Reference Example 2 above was cleaved using the restriction enzymes EcoR I and Pst I to obtain about 0.5 kb DNA fragment containing the region encoding human BFGF mutein.

Separately, the plasmid ptrp781 [Kurokawa, T. et al., Nucleic Acids Research, 11, 3077-3085 (1983)] DNA containing a trp promoter was cleaved using EcoR I-PsiI to yield in approximately 3.2 kb DNA fragment containing the trp promoter, a tetracycline resistance gene and a plasmid replication initiation site. The above-mentioned 0.5kb EcoRI-PstI DNA fragment containing the gene region encoding human bFGF mutein and this 3.2 kb DNA fragment were ligated together by T4 DNA ligase reaction to construct the plasmid pTB762 for human bFGF mutein expression.

Using this plasmid pTB762, Escherichia coli MM294 was transformed, whereby the strain Escherichia coli MM294/pTB762 (IFO 14613, FERM BP-1645) was obtained, which harbors the plasmid pTB762 containing the mutein CS23-encoding gene.

(2) Preparation of bacterial cell extract

The above-mentioned transformant was cultured in an M9 medium containing 1% glucose, 0.4% casamino acid and 8 μg/ml tetracycline, and, when Klett value became about 200, 3β-indolylacrylic acid was added to a concentration of 25 μg/ml, and this was followed by cultivation for 4 more hours. After cultivation, bacterial cells were collected, and were suspended in a 10% sucrose solution containing 20 mM Tris-HCl (pH 7.6), whose amount being 1/20 relating to the amount of the cultured broth. To this suspension were added phenylmethylsulfonyl fluoride (PMSF) to 1 mM, EDTA to 10 mM, NaCl to 0.1M, spermidine hydrochloride to 10 mM and lysozyme to 100 μg/Ml (every figure shows the final concentration), and the mixture was left at 0° C. for 45 minutes, after which it was subjected to ultrasonication for 30 seconds. This solution was centrifuged at 18,000 rpm (Sorval centrifuge, SS34 rotor) for 30 minutes to give a supernatant, which was then used as a bacterial cell extract.

(3) Human BFGF activity of the bacterial cell extract

Mouse BALB/c3-T3 cells, in an aliquots of $2\times10^3$ cells per well, were inoculated into 0.2 ml DMEM (Dulbecco's modified Eagle's medium [Virology 8, 396 (1959)]) containing 5% calf serum on Nunc 96-well microtiter plate (flat base) with each well containing 0.2 ml of the medium, and were cultured. The next day the medium was replaced with DMEM containing 0.5% calf serum. After 3 days of cultivation, 10 μl of the bacterial cell extract, previously serially diluted in 5-fold steps with DMEM containing 0.5% BSA, was added to each well, and was cultured. Twenty hours later, 2 μl of thymidine (hereinafter $^3$H-Tdr) (5 Ci/mmol, 0.5 mCi/ml RCC Amersham) was added to each well. Six hours later, cells were stripped by treatment with a phosphate-buffered solution (PBS) containing 0.2% trypsin-0.02% EDTA, and the cells were harvested onto glass filters by means of a Titertech cell harvester, whereafter the amount of $^3$H-Tdr taken up by the cells was determined using a scintillation counter.

As a result, the bacterial cell extract from E coli MM294/pTB762 exhibited FGF activity.

The rhbFGF mutein CS23, in which Cys at the 70 and 88-positions of human bFGF had been replaced by Ser, was thus obtained.

(4) A 25-ml extract obtained in (3) above (prepared from 500 ml of culture broth) was passed through a column (2 cm dia.×10 cm) of DEAE cellulose (DE52, Whatman, UK) equilibrated with 20 mM Tris-HCl, pH 7.4, in a 0.2 M NaCl solution to remove the nucleic acid components from the extract. The effluent from the column and the column washings with 20 mM Tris-HCl, pH 7.4, in a 0.2 M NaCl solution were combined (60 ml of the fraction passed through the DEAE).

This fraction was subjected to high performance liquid chromatography (Gilson, France) on a heparin column Shodex AF-pak HR-894 (8 mm ID×5 cm, produced by Showa Denko, Japan). The column was washed with the sequential addition of a 20 mM Tris-HCl solution, pH 7.4, and 20 mM TrisHCl, pH 7.4, in a 0.5 M NaCl solution, after which it was subjected to linear gradient elution (60 ml volume, 1.0 ml/min flow rate) with a gradient of 0.5 M to 2 M NaCl in a buffer of 20 mM Tris-HCl, pH 7.4.

The peak fraction eluted between 15 and 25 min of elution time was found to contain rhb FGF mutein CS23; this fraction was collected. The fraction's specific activity was 1.1 mg-protein FGF/mg protein, as calculated on the basis of the FGF activity of the standard sample of bovine brain-derived FGF (over 95% purity) produced by Takara Shuzo Co., Ltd., Japan.

REFERENCE EXAMPLE 4

Preparation of sodium salt of β-cyclodextrin tetradecasulfate (a) 5 g of β-cyclodextrin was dissolved in 250 ml dimethylformamide. To this solution, 15 g of sulfur trioxide-trimethylamine complex salt was added over a period of 5 min while stirring the solution at 70° C., and this was followed by 16 hr of agitation at constant temperature. After cooling the mixture, 250 ml of ethanol was added, and this was followed by decantation to collect insoluble material, which was then washed with a small amount of ethanol. The residue was dissolved in 250 ml water and the insoluble materials were filtered. To the filtrate, 75 ml of an aqueous solution of 30 w/v% sodium acetate was added, and this was followed by 1 hr of agitation at room temperature.

(b) The reaction mixture obtained above, containing sodium salt of β-cyclodextrin tetradecasulfate, was concentrated to dryness under reduced pressure. The concentrate was dissolved in 75 ml water. To this solution, 150 ml ethanol was added, and the gummy solid was collected by decantation. The gummy solid was powdered by addition of 30 ml ethanol, after which it was collected by filtration and dried to give 10.3 g of the subject compound.

Elemental analysis (as $C_{42}H_{56}O_{77}S_{14}Na_{14}$): Calculated: C, 19.68; H, 2.20; S, 17.51 (%) Found: C, 20.67; H, 3.40; S, 16.29 (%)

$[\alpha]_D + 83.5°$ (c=1.55, water)

Water content: 1.5 %w/w (Karl Fischer's method)

REFERENCE EXAMPLE 5

2.5 g of β-1,3-glucan (curdlan) with an average degree of polymerization of 540 was suspended in 100 ml of dimethylformamide. To this suspension, 12.5 g of trimethylamine-sulfonic acid synthesized from 13.5 g of chlorosulfonic acid and 11.7 g of triethylamine, was added, and this was followed by 24 hr of reaction in an ice water bath while stirring the mixture. The reaction mixture was sufficiently dialyzed against 0.5 M ammonium bicarbonate for 24 hrs and then against distilled water for 48 hrs, after which it was lyophilized to give 4.4 g of the desired product. The ammonium salt of β-1,3-glucan sulfate thus obtained had an average degree of substitution (DS) of 1.04 (sulfate content 12.7 %).

REFERENCE EXAMPLE 6

2.5g of β-1,3-glucan low molecular weight polymer (average degree of polymerization 6), obtained by partial hydrolysis (95° C., 40 min) of β-1, 3-glucan with an average degree of polymerization of 540 with 90% formic acid, was suspended in 150 ml of dimethylformamide. To this suspension, 50 g of triethylamine-sulfonic acid was added, and this was followed by 24 hr of reaction in an ice water bath while stirring the mixture. The reaction mixture was subjected to gel filtration through a column of 2.5 l Sephadex G-25 (fine) equilibrated with 0.02 M ammonium bicarbonate. The eluate was analyzed for sugar content by the phenolsulfonic acid method. The sugar fractions were then combined together and lyophilized to give 5.6 g of β-1,3-glucan sulfate. The desired product thus obtained had a DS of 1.12 (sulfur content 13.3%).

REFERENCE EXAMPLE 7

2.5g of a β1,3-glucan low molecular weight polymer (average degree of polymerization 26), obtained by partial hydrolysis (90° C., 40 min) of β-1, 3-glucan with an average degree of polymerization of 540 with 90% formic acid, was suspended in 150 ml of dimethylformamide. To this suspension, 50 g of triethylamine-sulfonic acid was added, and this was followed by 24 hr of reaction in an ice water bath while stirring the mixture. The reaction mixture was treated in the same manner as in Reference Example 6 to give 6.1 g of ammonium salt of β-1, 3-glucan sulfate. The desired product thus obtained had a DS of 1.22 (sulfur content 14.0 %).

REFERENCE EXAMPLE 8

2.5 g of a β-1,3-glucan low molecular weight polymer (average degree of polymerization 131), obtained by partial hydrolysis (80° C., 30 min) of β-1,3-glucan with an average degree of polymerization of 540 with 85% formic acid, was suspended in 100 ml of dimethylformamide. To this suspension, 12.5 g of triethylamine-sulfonic acid was added, and this was followed by 24 hr of reaction in an ice water bath while stirring the mixture. The reaction mixture was sufficiently dialyzed against 0.5 M ammonium bicarbonate for 24 hrs and then against distilled water for 48 hrs, after which it was lyophilized to give 3.9 g of ammonium salt of β-1, 3-glucan sulfate. The desired product thus obtained had a DS of 1.46 (sulfur content 15.4%).

REFERENCE EXAMPLE 9

The determination of FGF activity in the working examples presented below was done in accordance with a method described in (1) or (2) below. (1) Mouse BALB/c-3T3 cells, suspended in DAXEM ontaining 5% calf serum, were seeded into a Nune 96-well microtiter plate (flat base) in an amount of 0.2 ml ($2 \times 10^3$ cells) per well and cultivated. The next day the medium was replaced with DMEM containing 0.5% calf serum. After three days of cultivation, 10 μl of the bacterial cell extract, previously serially diluted 5-fold with DMEM containing 0.5% BSA, was added to each well and cultivated. Twenty hours later, 2 μl of $^3$H-Tdr (5 Ci/mmol, 0.5 mCi/ml RCC Amersham) was added to each well. Six hours later, cells were stripped by treatment with a phosphate buffer solution (PBS) containing 0.2% trypsin-0.02% EDTA, and the cells were harvested onto a glass filter by means of a Titertech cell harvester, whereafter the amount of $^3$H-Tdr taken in the cells was determined using a scintillation counter.

(2) The sample, previously diluted in 2-fold steps with DMEM containing 10% calf serum, was added to a Nune 96-well microriter plate (flat base) in an amount of 50 μl per well, whereafter fetal bovine heart endothelial cells (CRL1395) purchased from the American Type Culture Collection were seeded in an amount of 50 μl ($2 \times 10^3$ cells) per well and cultivated for 3 days. An MTT [3-(4,5-dimethylthiazolyl-2-yl)-2,5-diphenyltetrazolium bromide][Journal of Immunological Methods, 93 157–165 (1986)] solution (5 mg/ml PBS, Sigma) was then added in an amount of 20 μl per well. 4.5 hours later, 100 μl of 10% SDS-0.01 N HCl was added, and the plate was left in an incubator overnight, whereafter the absorbance at 590 nm was determined using a Titertech Multiscan [Tada et al.; Journal of Immunological Methods, 93,157(1986)].

EXAMPLE 1

To DMEM containing 10% fetal calf serum was added rhbFGF to have the concentration of the latter reach 10 μg/ml, to which was further added a salt of dextran sulfate to have the final concentration of the latter reach 25 μg/ml, and the medium was incubated at 37° C. for 24 hours. The salts of dextran sulfate were sodium salts whose average molecular weight was 5,000, 7,500 or 500,000, respectively. As a control group, the medium without dextran sulfate sodium was employed. The remaining activities after 24 hours are shown in Table 2. In the control, no substantial FGF activity remained, while, in the test groups, the FGF activity remained stable.

TABLE 2

| Additive | Remaining FGF activity (%) |
|---|---|
| Dextran sulfate sodium (average molecular weight 5,000) | 100 |
| Dextran sulfate sodium (average molecular weight 7,500) | 100 |
| Dextran sulfate sodium (average molecular weight 500,000) | 100 |
| none | 4 |

EXAMPLE 2

To DMEM containing 10% fetal calf serum was added rhbFGF mutein CS23 to have the concentration of the latter reach 10 μg/ml, to which was further added a salt of dextran sulfate so that the final concentration of the latter reached 25 μg/ml, and the medium was incubated at 37° C. for 24 hours. The salts of dextran sulfate were sodium salts whose average molecular weight were 5,000, 7,500 or 500,000, respectively. As a control group, the same medium, to which no dextran sulfate sodium was added, was employed. The remaining activities after 24 hours are shown in Table 3. In the control, no substantial activity remained, while in the test groups, the FGF activity remained essentially stable.

TABLE 3

| Additive | Remaining FGF activity (%) |
|---|---|
| Dextran sulfate sodium (average molecular weight 5,000) | 93 |
| Dextran sulfate sodium (average molecular weight 7,500) | 100 |
| Dextran sulfate sodium (average molecular weight 500,000) | 100 |
| none | 6 |

EXAMPLE 3

To a 20 mM phosphate buffer solution (pH 7.4) was added rhbFGF to have the concentration of the latter reach 10 μg/ml, to which was further added a dextran sulfate sodium (average molecular weight 7,500; Sulfur content 17.4%) at various ratios, followed by incubation at 37° C. for 72 hours. The amount of dextran sulfate sodium to be added was such that its concentration reached 0 to 16 mol. relative to rbhFGF. As the control, the same medium containing no dextran sulfate was employed. Remaining activities after 72 hours are shown in Table 4.

TABLE 4

| Molar ratio of rhbFGF/ dextran sulfate sodium | Remaining FGF activity (%) |
|---|---|
| 1:0 | <3 |
| 1:0.25 | 15 |
| 1:1 | 99 |
| 1:4 | 95 |
| 1:16 | 100 |

EXAMPLE 4

To a 20 mM buffer solution (pH 7.4) was added rhbFGF to have the concentration of the latter reach 10 μg/ml, to which were further added dextran sulfate sodium and/or sodium citrate, followed by freeze-drying. The final concentration of dextran sulfate sodium (average molecular weight 7,500; S content 17.4%) was 25 μg/ml, while that of sodium citrate was 50 mM. The freeze-dried materials were restored by the addition of distilled water, which were then subjected to determination of remaining activities. The results are shown in Table 5.

TABLE 5

| Additive | Remaining FGF activity (%) |
|---|---|
| Dextran sulfate sodium | 100 |
| Sodium citrate | 48 |
| Dextran sulfate sodium + sodium citrate | 97 |
| none | 6 |

EXAMPLE 5

To a 20 mM phosphate buffer solution (pH 7.4) was added rhbFGF to have the concentration of the latter reach 10 μg/ml, to which was further added dextran sulfate sodium (average molecular weight 7,500; Sulfur content 17.4%) to have the final concentration of the latter reach 25 μg/ml, followed by incubation at 37° C. for 72 hours. On the other hand, in place of the above-mentioned dextran sulfate sodium, sodium citrate, sodium malate, sodium maleate, sodium fumarate or sodium tartrate was added to the above-mentioned buffer solution to have the final concentration reach 0.4 M, singly or in admixture of dextran sulfate sodium (25 μg/ml), followed by incubation at 37° C. for 24 hours. The remaining activities after 72 hours are shown in Table 6.

TABLE 6

| Additive | Remaining FGF activity (%) |
|---|---|
| Dextran sulfate sodium | 91 |
| Sodium citrate | 72 |
| Sodium citrate + dextran sulfate sodium | 100 |
| Sodium malate | 40 |
| Sodium malate + dextran sulfate sodium | 93 |
| Sodium maleate | 54 |
| Sodium maleate + dextran sulfate sodium | 94 |
| Sodium fumarate | 35 |
| Sodium fumarate + dextran sulfate sodium | 90 |
| Sodium potassium tartrate | 63 |
| Sodium potassium tartrate + dextran sulfate sodium | 97 |

TABLE 6-continued

| Additive | Remaining FGF activity (%) |
|---|---|
| none | 2 |

EXAMPLE 6

To a 50 mM sodium citrate solution, pH 7.4, rhbFGF was added to 100 μg/ml concentration. To this mixture, a salt of dextran sulfate was added to a final concentration of 46 μg/ml (1:1 molar ratio), and this was followed by 30 min of incubation at 56° C. The salt of dextran sulfate used was in the form of a sodium salt, having an average molecular weight of 7,500. A group not supplemented with dextran sulfate was established as the control. Table 7 shows the remaining activity found 30 min later. As is evident from the results shown in Table 7, FGF activity was almost lost in the control group, while FGF activity remained stable even at a high temperature in the dextran sulfate group.

TABLE 7

| Additive | Remaining FGF activity (%) |
|---|---|
| Dextran sulfate sodium (average molecular weight 7,500) | 100 |
| Not added | 11 |

EXAMPLE 7

To a 2 mM phosphate buffer solution (pH 7.0), rhbFGF mutein CS23, as obtained in Reference Example 3, was added to 100 μg/ml concentration. To this mixture, dextran sulfate sodium with an average molecular weight of 7,500 was added to a final concentration of 46 μg/ml (1:1 molar ratio) and this was followed by 2 hr incubation at 37° C. at pH 3.0, 5.0, 7.4 or 9.7. Table 8 shows the remaining FGF activity found after 2 hr incubation.

As is evident from the results shown in Table 8, FGF activity showed a noticeable decrease at any pH in the control group, but FGF activity was sustained at a high level in the dextran sulfate group.

TABLE 8

| Additive | pH | Remaining FGF activity (%) |
|---|---|---|
| Dextran sulfate sodium | 3.0 | 80 |
| Dextran sulfate sodium | 5.0 | 100 |
| Dextran sulfate sodium | 7.4 | 100 |
| Dextran sulfate sodium | 9.7 | 87 |
| Not added | 3.0 | 30 |
| Not added | 5.0 | 45 |
| Not added | 7.4 | 60 |
| Not added | 9.7 | 28 |

EXAMPLE 8

To 8 mM HCl, rhbFGF mutein CS23, as obtained in Reference Example 3, and dextran sulfate sodium with an average molecular weight of 7,500 were added to final concentrations of 100 μg/ml and 94 μg/ml, respectively (1:1 molar ratio), whereafter pepsin was added to 4 μg/ml concentration (final pH 2.1). A group not supplemented with dextran sulfate sodium was used as the control. The reaction mixture was incubated at 37° C. for 30 min, and remaining FGF activity was determined (Table 9). Almost all rhbFGF mutein CS23 activity was lost in the control group, but FGF activity remained stable with regards to pepsin digestion in the dextran sulfate sodium group.

TABLE 9

| Additive | Remaining FGF activity (%) |
|---|---|
| Dextran sulfate sodium | 98 |
| Not added | 2 |

EXAMPLE 9

To a 20 mM phosphate buffer solution (pH 7.4), rhbFGF mutein CS23, as obtained in Reference Example 3, was added to 100 μg/ml concentration. To this mixture, dextran sulfate sodium with an average molecular weight of 7,500 was added to 94 μg/ml (1:1 molar ratio) concentration, whereafter trypsin or α-chymotrypsin was added to 4 μg/ml concentration. This was followed by incubation at 37° C. for 16 hours. A group not supplemented with dextran sulfate sodium was used as the control. Almost all rhbFGF mutein CS23 activity was lost in the control group, but activity remained stable in the presence of a protease such as trypsin or α-chymotrypsin in the dextran sulfate sodium group (Table 10).

TABLE 10

| Enzyme | Additive | Remaining FGF activity (%) |
|---|---|---|
| Trypsin | Dextran sulfate sodium | 95 |
| Trypsin | Not added | 4 |
| α-chymotrypsin | Dextran sulfate sodium | 92 |
| α-chymotrypsin | Not added | 6 |

EXAMPLE 10

To DMEM containing 10% fetal bovine serum, rhbFGF was added to μg/ml concentration. To this mixture, β-cyclodextrin tetradecasulfate sodium, as obtained in Reference Example 4, or β-1,3-glucan sulfate ammonium, as obtained in Reference Examples 5 through 8, was added to a final concentration of 500 μg/ml, and this was followed by 24 hr of incubation at 37° C. The β-1, 3-glucan sulfate ammonium used had an average degree of polymerization of 6 (sulfur content 13.5%), 26 (sulfur content 14.0%), 131 (sulfur content 15.4%) or 540 (sulfur content 12.7%). A group not supplemented with sulfated glucan was established as the control group. Table 11 shows remaining FGF activity found after 24 hr of incubation. Almost all FGF activity was lost in the control group, but FGF activity remained stable in the β-cyclodextrin sulfate or β-1, 3-glucan sulfate group.

TABLE 11

| Additive | Remaining FGF activity (%) |
|---|---|
| β-cyclodextrin tetradecasulfate sodium | 100 |
| β-1,3-glucan sulfate ammonium (average degree of polymerization 6) | 75 |
| β-1,3-glucan sulfate ammonium (average degree of polymerization 26) | 100 |
| β-1,3-glucan sulfate ammonium (average degree of polymerization 131) | 100 |
| β-1,3-glucan sulfate ammonium (average degree of polymerization 540) | 100 |
| None | 4 |

EXAMPLE 11

To Dulbecco's MEM medium containing 10% fetal bovine serum, rhbFGF mutein CS23 was added to 10 μg/ml concentration. To this mixture, β-cyclodextrin tetradecasulfate sodium, as obtained in Reference Example 4, or β-1, 3-glucan sulfate ammonium, as obtained in Reference Example 5 through 8, was added to a final concentration of 500 μg/Ml. This was followed by 24 hr of incubation at 37° C. The β-1,3-glucan sulfate ammonium used had an average degree of polymerization of 6 (sulfur content 13.5%), 26 (sulfur content 14.0%), 131 (sulfur content 15.4%) or 540 (sulfur content 12.7%). A group not supplemented with sulfated glucan was established as the control group. Table 12 shows remaining FGF activity found after 24 hr of incubation. Almost all FGF activity was lost in the control group, but FGF activity remained stable in the β-cyclodextrin sulfate or β-1, 3-glucan sulfate group.

TABLE 12

| Additive | Remaining FGF activity (%) |
|---|---|
| β-cyclodextrin tetradecasulfate sodium | 100 |
| β-1,3-glucan sulfate ammonium (average degree of polymerization 6) | 100 |
| β-1,3-glucan sulfate ammonium (average degree of polymerization 26) | 100 |
| β-1,3-glucan sulfate ammonium (average degree of polymerization 131) | 100 |
| β-1,3-glucan sulfate ammonium (average degree of polymerization 540) | 100 |
| None | 6 |

EXAMPLE 12 rhbFGF mutein CS23, as obtained in Reference Example 3 (980 μg/ml), and dextran sulfate sodium, with an average molecular weight of 7500 (45 mg/ml), in a ratio by volume of 1 to 1, were mixed together. A 200 μl aliquot of the composition was loaded onto a column (0.75 × 60 cm) of TSK-gel 3000SW (Tosoh, Ltd. Japan) and the protein was eluted with a 0.1 M phosphate buffer solution (pH 6.0) containing 0.1 M $Na_2SO_4$. The flow rate was 1.0 ml/min. Proteins were monitored at 230 nm. The mixture gave two peaks (see FIG. 2): peak I (indicated by I) and peak II (indicated by II). The two peaks were each collected and analyzed; peak I proved to be a complex containing rhbFGF mutein CS23 and dextran sulfate sodium in a 1:4 ratio, and peak III dextran sulfate sodium.

The molecular weight of the above complex was estimated as approximately 45,000 from FIG. 2.

EXAMPLE 13

A stable injectable aqueous solution (pH 7.4) containing rhbFGF, 0.5 mg; dextran sulfate sodium, 0.23 mg; sodium citrate, 15 mg was prepared.

EXAMPLE 14

A stable injectable aqueous solution (pH 7.4) containing rhbFGF mutein CS23, 0.5 mg; dextran sulfate sodium, 0.23 mg; sodium citrate, 15 mg was prepared.

What we claim is:

1. A stabilized composition which comprises fibroblast growth factor (FGF) or a mutein consisting of a deletion mutein of FGF and a substitution mutein of FGF which exhibits pharmacological or physiological activities similar to those of FGF and a stabilizing amount of a glucan sulfate.

2. The composition according to claim 1, wherein said FGF or mutein of FGF is acidic or basic FGF or a mutein of acidic or basic FGF.

3. The composition according to claim 2, wherein said FGF or said mutein of FGF is complexed with said glucan sulfate at a ratio from about 1:0.5 to about 1:5.

4. The composition according to claim 1 which comprises said mutein of FGF and glucan sulfate.

5. The composition according to claim 1, wherein said FGF or mutein of FGF is produced by recombinant DNA technology.

6. The composition according to claim 5, comprising a mutein of human basic FGF.

7. The composition as claimed in claim 6, wherein one to four constituent cysteine is replaced by a neutral amino acid.

8. The composition according to claim 7, wherein the mutein of FGF is recombinant human basic FGF mutein CS23.

9. The composition according to claim 1, wherein the glucan sulfate has sulfur content of about 12 to 20% (w/w).

10. The composition according to claim 1, wherein the glucan sulfate is dextran sulfate.

11. The composition according to claim 1, wherein the glucan sulfate is cyclodextrin sulfate.

12. The composition according to claim 1, wherein the glucan sulfate is β-1,3-glucan sulfate.

13. The composition according to claim 1 which further comprises a di- or tri-basic carboxylic acid.

14. A pharmaceutical composition comprising the stabilized composition of claim 1 and a pharmaceutically acceptable carrier.

15. The composition according to claim 14 wherein the composition is in an injection aqueous solution.

* * * * *